(12) United States Patent
Jeong et al.

(10) Patent No.: US 10,195,266 B2
(45) Date of Patent: Feb. 5, 2019

(54) VERSATILE INFLUENZA VIRUS VACCINE COMPOSITION

(71) Applicant: KOREA RESEARCH INSTITUTE OF BIOSCIENCE AND BIOTECHNOLOGY, Daejeon (KR)

(72) Inventors: Dae Gwin Jeong, Daejeon (KR); Dae Sub Song, Sejong (KR); Sun Woo Yoon, Daejeon (KR)

(73) Assignee: KOREA RESEARCH INSTITUTE OF BIOSCIENCE AND BIOTECHNOLOGY, Daejeon (KR)

( * ) Notice: Subject to any disclaimer, the term of this patent is extended or adjusted under 35 U.S.C. 154(b) by 0 days.

(21) Appl. No.: 15/574,274

(22) PCT Filed: Sep. 14, 2015

(86) PCT No.: PCT/KR2015/009618
§ 371 (c)(1),
(2) Date: Nov. 15, 2017

(87) PCT Pub. No.: WO2016/186260
PCT Pub. Date: Nov. 24, 2016

(65) Prior Publication Data
US 2018/0133305 A1    May 17, 2018

(30) Foreign Application Priority Data

May 18, 2015 (KR) .......................... 10-2015-0069106

(51) Int. Cl.
| | |
|---|---|
| *A61P 31/16* | (2006.01) |
| *C07K 14/11* | (2006.01) |
| *C07K 16/10* | (2006.01) |
| *A61K 39/145* | (2006.01) |
| *A61K 39/395* | (2006.01) |

(52) U.S. Cl.
CPC .......... *A61K 39/145* (2013.01); *A61K 39/395* (2013.01); *A61P 31/16* (2018.01); *C07K 14/11* (2013.01); *C07K 16/10* (2013.01); *C07K 16/1018* (2013.01)

(58) Field of Classification Search
CPC ................ A61K 39/145; A61K 39/395; C07K 16/1018; C07K 14/11; C07K 16/10; A61P 31/16
See application file for complete search history.

(56) References Cited

U.S. PATENT DOCUMENTS

2012/0014972 A1    1/2012   Hodges et al.

FOREIGN PATENT DOCUMENTS

| KR | 10-2010-0137804 A | 12/2010 |
|---|---|---|
| KR | 10-2014-0010583 A | 1/2014 |

OTHER PUBLICATIONS

Krammer F, Palese P. Influenza virus hemagglutinin stalk-based antibodies and vaccines. Curr Opin Virol. Oct. 2013;3(5):521-30. Epub Aug. 24, 2013.*
Anette Schneemann, et al., "A Virus-Like Particle that Elicits Cross-Reactive Antibodies to the Conserved Stem of Influenza Virus Hemagglutinin", Journal of Virology, Nov. 2012, pp. 11686-11697, vol. 86, No. 21.
X Fan, et al., "Targeting the HA2 subunit of influenza a virus hemagglutinin via CD40L provides universal protection against diverse subtypes", Mucosal Immunology, Jan. 2015, pp. 211-220, vol. 8, No. 1.
International Search Report for PCT/KR2015/009618 dated Dec. 10, 2015 [PCT/ISA/210].

* cited by examiner

*Primary Examiner* — Rachel B Gill
(74) *Attorney, Agent, or Firm* — Sughrue Mion, PLLC

(57) ABSTRACT

The present invention relates to a versatile influenza virus vaccine composition using the HA2 helical domain of a hemagglutinin protein, which is an influenza surface protein, and to a pharmaceutical composition for preventing or treating influenza virus infectious diseases. The polypeptide expressed by SEQ ID NO: 3 and the polypeptide expressed by residues 379 to 474 of SEQ ID NO: 1 of the present invention can be mass-produced in *E. coli*, and effectively produce neutralizing antibodies to various influenza virus subtypes, and thus the polypeptides can be widely utilized as versatile vaccines for influenza virus subtypes and new influenza virus variants.

11 Claims, 6 Drawing Sheets

Specification includes a Sequence Listing.

Fig. 1

H1HA trimerization → H1HA single → Stem helical domain → Triple stem helical domain

VERSATILE INFLUENZA VIRUS VACCINE COMPOSITION

CROSS REFERENCE TO RELATED APPLICATIONS

This application is a National Stage of International Application No. PCT/KR2015/009618, filed on Sep. 14, 2015, which claims priority from Korean Patent Application No. 10-2015-0069106, filed on May 18, 2015, the contents of all of which are incorporated herein by reference in their entirety.

The instant application contains a Sequence Listing which has been filed electronically in ASCII format and is hereby incorporated by reference in its entirety. Said ASCII copy, created on Aug. 16, 2018, is named Q236580_SL.txt and is 36,400 bytes in size.

TECHNICAL FIELD

The present invention relates to a versatile influenza virus vaccine composition and a pharmaceutical composition for preventing or treating influenza infectious disease using an HA2 helical domain of hemagglutinin protein, an influenza surface protein.

BACKGROUND ART

Influenza is an acute febrile illness caused by influenza virus respiratory infection. Influenza viruses are classified into A, B, and C types depending on differences in surface structural proteins. There are slight differences in host, epidemiology and clinical features among the types of influenza viruses. Influenza virus is a spherical virus with a diameter of 80-120 nm, whose subtypes are determined based on the type of hemagglutinin (HA) and neuraminidase (NA) glycoproteins exposed on the surface. Subtypes are classified mainly with regard to type A influenza. Currently, there have been found 16 types of HA from H1 to H16 and 9 types of NA from N1 to N9, and a total of 144 subtypes (for example, H1N1 and H1N2) exist in type A influenza even based on a simple calculation. Influenza causes new big and small epidemics every year through antigen variations. Antigen variations include antigenic shift (e.g., H3N2→H2N2) in which HA or NA is replaced with new HA or NA resulting in subtype alteration, and antigenic drift in which point mutations take place in existing HA and NA genes. Antigen drift, which occurs almost every year in influenza A or B type, causes seasonal epidemic.

Among HA and NA surface antigens, immunization against HA is particularly associated with influenza prevention and disease severity. Therefore, neutralizing antibodies produced in a body against hemagglutinin, which is the most important component of the influenza vaccine, play a crucial role in the prevention of influenza virus infection. Influenza vaccines include inactivated vaccines and live vaccines. The inactivated vaccine is made by purifying the viruses cultured in an embryonated egg and deactivating them with formalin or the like. The vaccines include a whole virus vaccine in which entire inactivated viruses are utilized, a split vaccine in which a viral envelopes are pulverized with ether etc., and a subunit vaccine in which hemagglutinin and neuramidase components are purified, etc. As for the live vaccine, a live attenuated influenza vaccine (LAIV) has been developed and used. Because the whole virus vaccine causes side effects in children, they are currently not used globally including Korea, but used only in some countries. On the other hand, component vaccines such as split vaccines and subunit vaccines are widely used due to their safety and acknowledged effectiveness. In addition, a vaccine containing an adjuvant such as MF-59 to enhance the immune response or a virosome vaccine which forms virus-like vesicles has been developed and used in some countries. Antibodies against specific influenza virus obtained through natural infection or vaccination do not form protective antibodies against influenza viruses of other subtypes and cannot exhibit sufficient immunogenicity against new variants of an antigen. Since influenza viruses have big and small mutations every year, the epidemic strain changes every year. Therefore, it is hard to expect the effect of the vaccination in the previous year, and the vaccination should be conducted every year.

Globally, influenza virus is a serious and constant threat to human health. Each year, 3 to 5 million people show severe symptoms by the infection and 500,000 people die, and a seasonal influenza epidemic could potentially kill millions. Antagonists to the virus surface glycoprotein, neuraminidase, have been widely used for the treatment of influenza infections, but their efficacy has been drastically decreased by drug-resistant viral mutants. Vaccine is the most effective way to prevent influenza virus infection, but as mentioned above, the protective efficacy of the vaccine is not optimized for high-risk groups such as patients with weak immunity, e.g., pediatric and elderly people. In addition, post-vaccination immunity typically responds specifically to a new variant, but the influenza virus rapidly changes, and thus, new vaccine should be produced almost every year. The determination of the antigenic composition of the vaccine is based on the anticipation of a variant that will be prevalent in the new year. Therefore, vaccines are ineffective if a vaccine variant is different from epidemic variant. As a result, there is desperate need for vaccines having new preventive and therapeutic effects that can exhibit broad protection against influenza viruses.

Immunization against influenza virus is mediated almost by neutralizing antibodies targeting hemagglutinin (HA). Identification of an antigenic position in hemagglutinin means to find the immunologically predominant hemagglutinin head domain (HA1) which mediates entry of influenza viruses into a host cell by attaching to sialic acid receptors. Studies using anti-HA head domain monoclonal antibodies indicate that this type of antibodies blocks the attachment of the virus to the sialic acid on the host cell surface, thereby preventing the virus from entering into the cell. However, due to high mutation rates and tolerance for antigenic changes in the hemagglutinin head domain, antibodies targeting the hemagglutinin head domain are only effective against very similar variants. As such, a broader range of antibodies targeting the receptor attachment site is not structurally discovered. In contrast, antibodies which are attached to the hemagglutinin stem domain (HA2) adjacent to the cell membrane block the major structural rearrangement of HA essential for the fusion of the viruses with the endosomal membranes of the host, thereby blocking the entry of the viruses into the cell. Amino acid sequences of the HA stem domain is relatively well conserved in various influenza strains due to less mutations than the head domain. However, due to the diversity of antigenic stimuli found in the hemagglutinin head domain, it is known that most monoclonal antibodies targeting the stem domain generally neutralize only specific single virus.

However, not many studies have been conducted yet on broadly versatile neutralizing monoclonal antibodies (bNAbs) that can neutralize various subtypes of influenza viruses. Therefore, there is a desperate need for a new vaccine that can be used as a broadly versatile vaccine for various subtypes.

DISCLOSURE OF INVENTION

Technical Problem

It is an object of the present invention to provide a novel influenza versatile vaccine which can exhibit effects against various influenza virus subtypes, thereby dealing with the advent of new influenza variants.

Accordingly, it is an object of the present invention to provide an antibody against a single HA2 helical domain or a trimerized HA2 helical domain of influenza hemagglutinin, an influenza virus vaccine composition and a pharmaceutical composition comprising the same.

It is yet another object of the present invention to provide a method for inducing influenza immunity.

Solution to Problem

In order to achieve the above object, the present invention provides a polypeptide represented by SEQ ID NO: 3.

In addition, the present invention provides a monoclonal antibody against a polypeptide represented by residues 379 to 474 of SEQ ID NO: 1 or a polypeptide represented by SEQ ID NO: 3.

In addition, the present invention provides an influenza virus vaccine composition comprising a polypeptide represented by residues 379 to 474 of SEQ ID NO: 1 or a polypeptide represented by SEQ ID NO: 3.

In addition, the present invention provides a pharmaceutical composition for preventing or treating an influenza infectious disease comprising the polypeptide represented by residues 379 to 474 of SEQ ID NO: 1 or the polypeptide represented by SEQ ID NO: 3.

In addition, the present invention provides a method for inducing influenza immunity comprising the step of administering to an individual the polypeptide represented by residues 379 to 474 of SEQ ID NO: 1 or the polypeptide represented by SEQ ID NO: 3.

Advantageous Effects of Invention

The polypeptide represented by SEQ ID NO: 3 and the polypeptide represented by residues 379 to 474 of SEQ ID NO: 1 of the present invention can be mass-produced in *E. coli*, and effectively produce neutralizing antibodies against various influenza virus subtypes, and thus, the polypeptides can be widely utilized as versatile vaccines for influenza virus subtypes and new influenza virus variants.

BRIEF DESCRIPTION OF DRAWINGS

Figure 1:
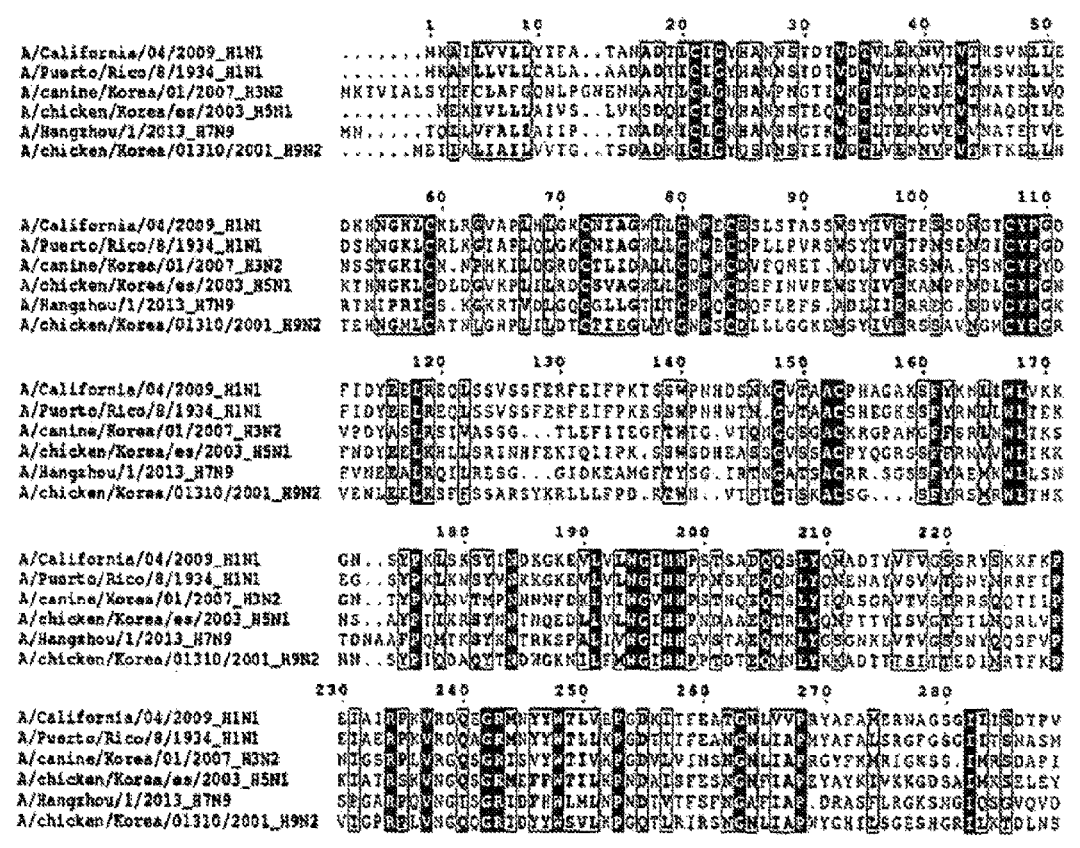

FIG. 1 shows the result of the amino acid sequence analysis of the hemagglutinin HA1 head domain using ESPript 3.0. FIG. 1 discloses residues 1-289 of SEQ ID NO: 1, residues 1-289 of SEQ ID NO: 5, residues 1-290 of SEQ ID NO: 6, residues 1-252 of SEQ ID NO: 7, residues 1-283 of SEQ ID NO: 8, and residues 1-283 of SEQ ID NO: 9, all respectively, in order of appearance.

FIG. 2 discloses residues 290-566 of SEQ ID NO: 1, residues 290-566 of SEQ ID NO: 5, residues 291-566 of SEQ ID NO: 6, residues 253-533 of SEQ ID NO: 7, residues 284-560 of SEQ ID NO: 8, and residues 284-560 of SEQ ID NO: 9, all respectively, in order of appearance.

BEST MODE FOR CARRYING OUT THE INVENTION

Figure 2:
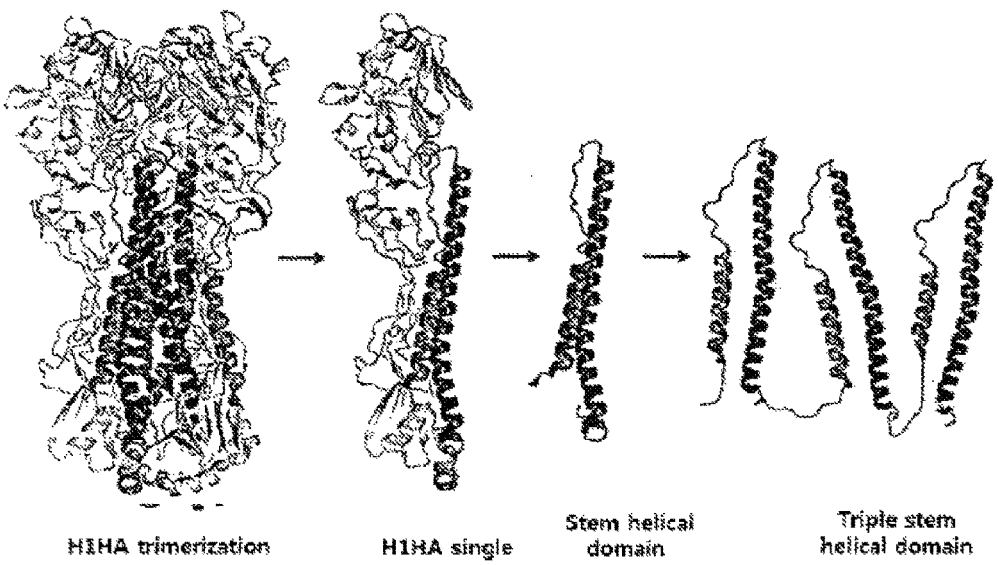
FIG. 2 depicts the result of the structure-based amino acid sequence analysis of hemagglutinin HA2 stem domain using ESPript 3.0 and the structure of its trimerized domain.
Figure 3:
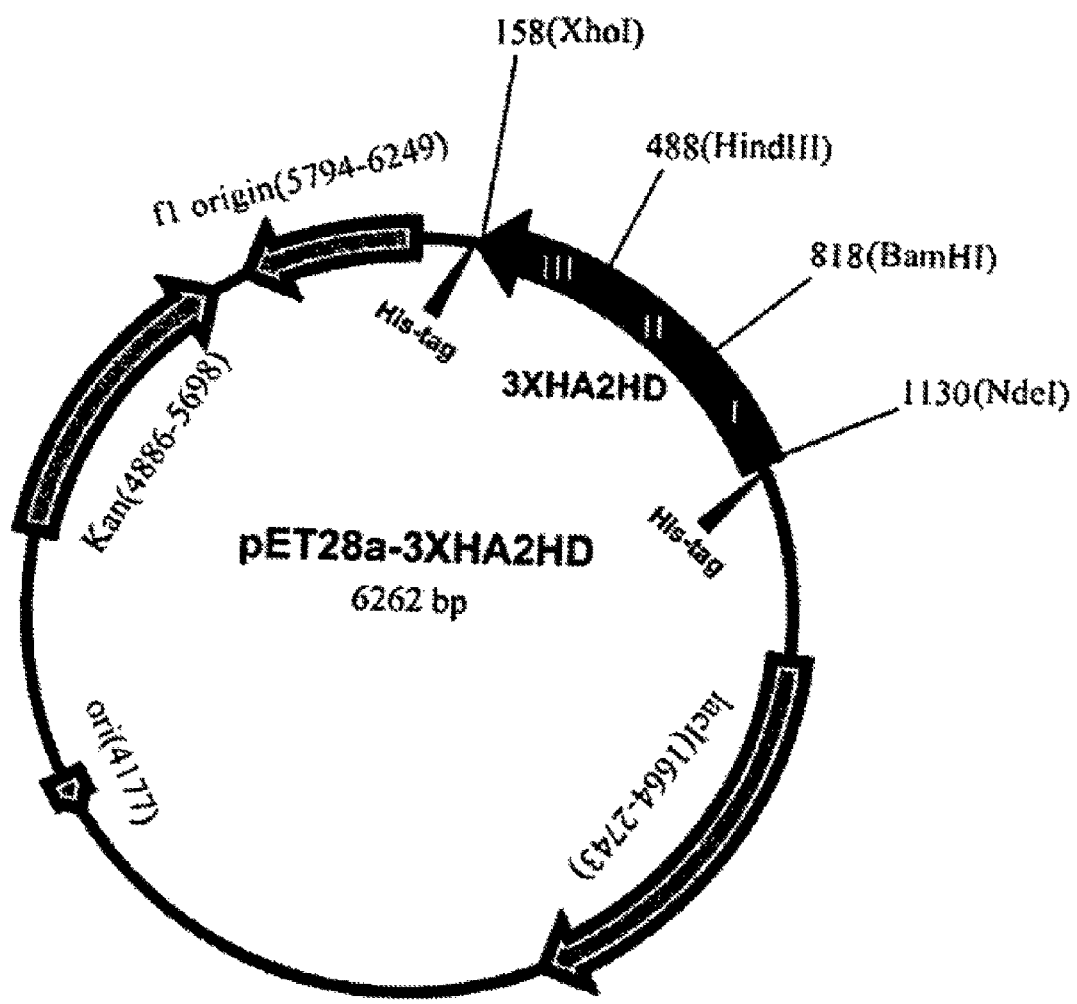
FIG. 3 illustrates the *E. coli* expression vector pET28a-3XHA2HD.
Figure 4A:
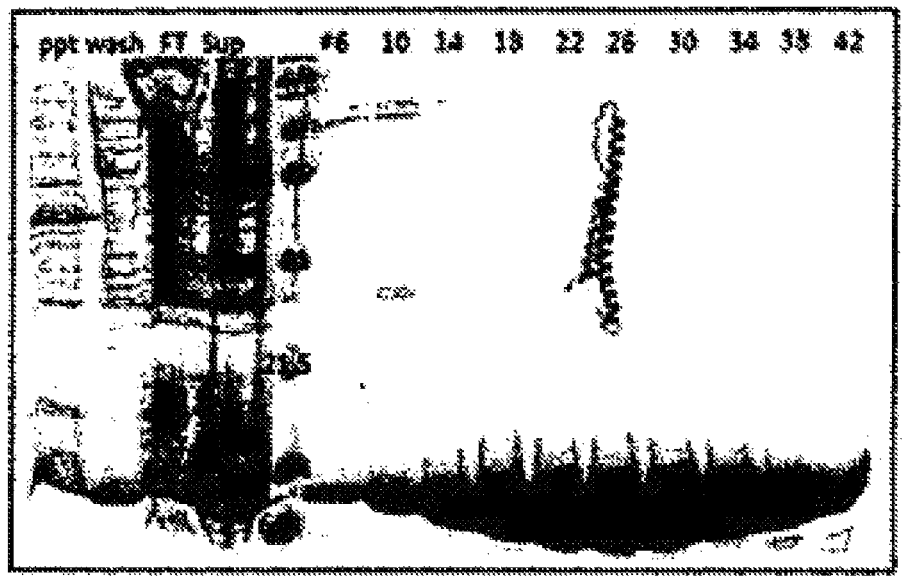
FIG. 4(A) and FIG. 4(B) demonstrate the results of identifying a single HA2 helical domain, and its trimerized helical domain using SDS-PAGE, respectively.
Figure 4B:
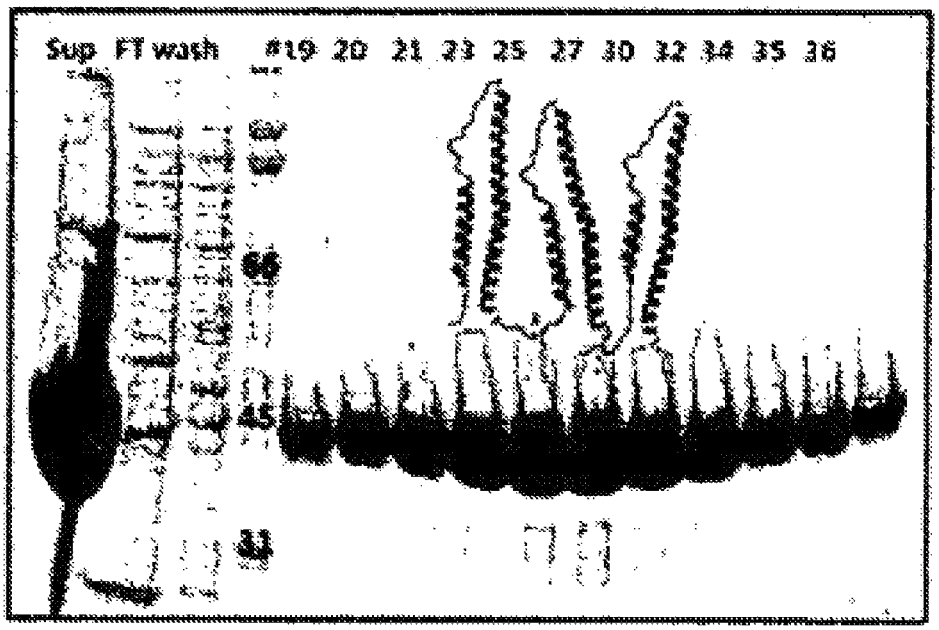
Figure 5:
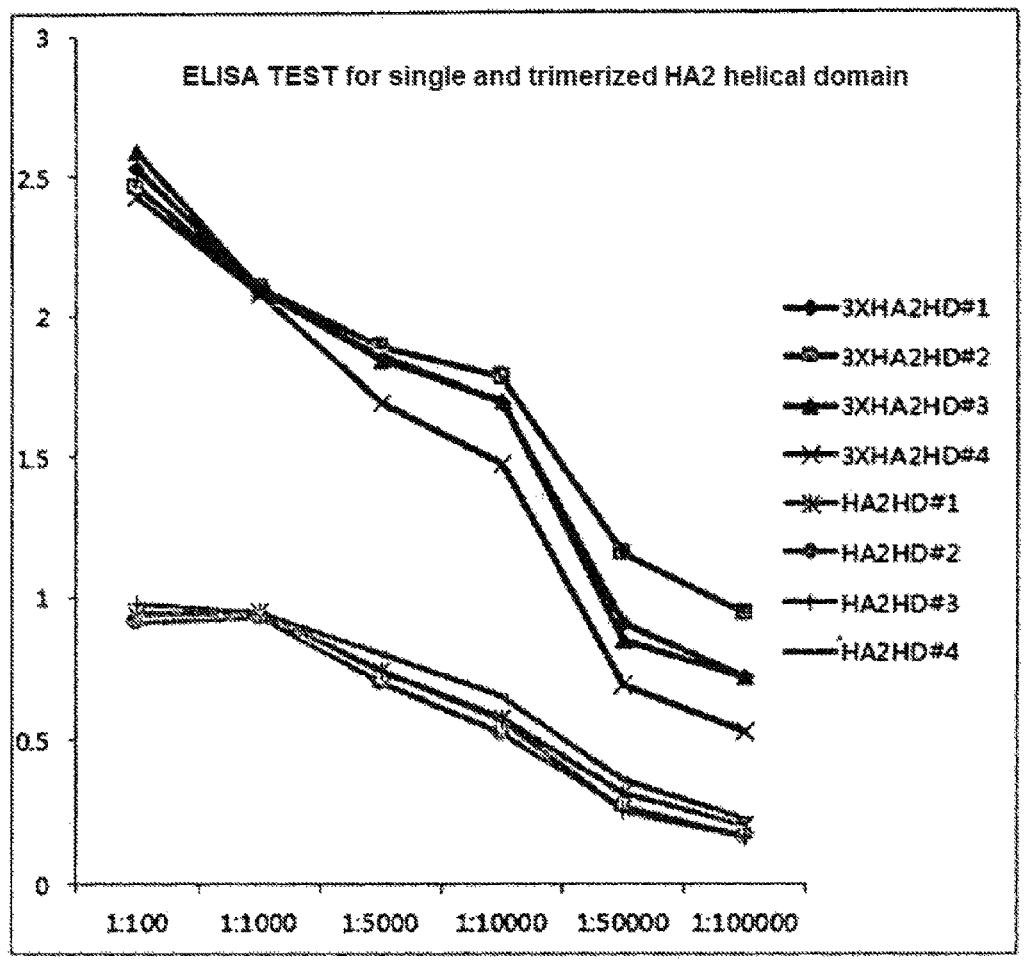
FIG. 5 is a graph presenting the results of identifying the immune antibody-forming effect of a single HA2 helical domain (HA2HD) and a trimerized HA2 helical domain (3XHA2HD) by ELISA test.

The present invention provides a polypeptide represented by SEQ ID NO: 3. In addition, the present invention provides an antibody against the polypeptide represented by residues 379 to 474 of SEQ ID NO: 1 or the polypeptide represented by SEQ ID NO: 3.

The polypeptide represented by residues 379 to 474 of SEQ ID NO: 1 and the polypeptide represented by SEQ ID NO: 3 of the present invention can effectively form a neutralizing antibody against various subtypes of influenza viruses such as H1, H3, H5, H7 and H9. In addition, the polypeptide may induce an antigen-antibody reaction by acting as an antigen in an individual, thereby inducing an immune response against influenza.

Hereinafter, the present invention will be described in detail.

"The polypeptide represented by residues 379 to 474 of SEQ ID NO: 1 or the polypeptide represented by SEQ ID NO: 3" of the present invention includes not only the same polypeptide but also polypeptides whose amino acids are substituted by conservative substitution, and polypeptides having a sequence homology of 80 to 99%, preferably 85 to 99%, more preferably 90 to 99%.

The term "conservative substitution" refers to the substitution of an amino acid of one class with an amino acid of the same class. Conservative substitutions do not alter the structure or function of the polypeptide, or neither of them. The amino acid classes for the purpose of conservative substitution include hydrophobic (e.g., Met, Ala, Val, Leu), neutral hydrophilic (e.g., Cys, Ser, Thr), acidic (e.g., Asp, Glu), basic (e.g., Asn, Gln, His, Lys, Arg), conformational disruptor (e.g., Gly, Pro) and aromatic (e.g., Trp, Tyr, Phe) classes.

The term "antigen" refers to an antigenic component capable of causing an immune response among the components of a virus, preferably a protein expressed by a virus. In a specific embodiment, the polypeptide represented by residues 379 to 474 of SEQ ID NO: 1 or the polypeptide of SEQ ID NO: 3 is derived from the hemagglutinin stem domain expressed by influenza virus, which can function as an antigen to induce an immune response when administered to an individual. Such antigens can be prepared from the base sequences of SEQ ID NO: 4 and SEQ ID NO: 2 by a method known in the art.

The present invention also provides an influenza virus vaccine composition comprising the polypeptide represented by residues 379 to 474 of SEQ ID NO: 1 or the polypeptide represented by SEQ ID NO: 3.

The "vaccine" induces an antigen-antibody reaction in an individual for the purpose of preventing or treating a common influenza virus.

The "polypeptide represented by residues 379 to 474 of SEQ ID NO: 1" refers to a single HA2 helical domain of the full-length sequence of influenza hemagglutinin.

In addition, the "polypeptide represented by SEQ ID NO: 3" refers to a trimerized HA2 helical domain of influenza hemagglutinin. Herein, the trimerized HA2 helical domain may consist of a fragment 1 of residues 379-480 of SEQ ID NO: 1, a fragment 2 of residues 373-480 of SEQ ID NO: 1, and a fragment 3 of residues 373-480 of SEQ ID NO: 1.

In addition, such fragments 1 to 3 of a trimerazed domain may include all of the polypeptides which are the same fragments described above, those which have conservative substitutions thereof, or those which have sequence homology of 80 to 99%, preferably 85 to 99%, more preferably 90 to 99%.

The polypeptide represented by SEQ ID NO: 3 may be encoded by the base sequence of SEQ ID NO: 2.

The "influenza virus" is classified into influenza virus types of A, B and C. The term "influenza virus subtype" as used herein refers to an influenza A virus variant characterized by a combination of hemagglutinin (H) and neuramidase (N) viral surface proteins. According to the present invention, influenza virus subtypes may be referred to based on the H number, such as, for example "influenza virus comprising HA of H3 subtype," "influenza virus of H3 subtype" or "H3 influenza", or based on the combination of H number and N number, such as, for example, "influenza virus of subtype H3N2" or "H3N2 influenza virus." The term "subtype" specifically includes all individual "strains" within each subtype which generally result from mutation. In addition, the subtypes include naturally isolated strains and artificial mutants or rearrangements, and exhibit different pathological profiles. Such strains may also be referred to as the various "isolated strains" of viral subtypes. Thus, the terms "strain" and "isolated strain" may be used interchangeably.

The vaccine of the present invention can effectively induce the formation of neutralizing antibodies against various subtypes of influenza viruses. Preferably, it can induce the formation of neutralizing antibodies against at least one influenza virus subtype selected from the group consisting of H1, H3, H5, H7 and H9. All of the antibodies thus formed can bind to hemagglutinin of various subtypes of influenza viruses. More preferably, it can bind to the subtypes such as pH1N1, cH3N2, hH3N2, aH5N1, dH7N9.

Accordingly, the present invention provides an influenza virus vaccine composition comprising the polypeptide represented by residues 379 to 474 of SEQ ID NO: 1 or the polypeptide represented by SEQ ID NO: 3. The virus may be of at least one influenza virus subtype selected from the group consisting of H1, H3, H5, H7 and H9.

The present invention also provides a vaccine composition wherein the vaccine is a versatile vaccine.

The term "versatile vaccine" refers to a vaccine with a broad range of applications that can neutralize all influenza viruses including influenza virus subtypes and novel variants thereof.

The vaccine of the present invention may be at least one selected from the group consisting of a subunit vaccine, a synthetic vaccine, and a genetically engineered vaccine.

The term "subunit vaccine" refers to a vaccine prepared by extracting only an antigen component capable of causing an immune function among the components of a virus. The subunit vaccine can minimize side effects by inducing immunity formation only against the site of the antigen necessary for viral defense.

The term "synthetic vaccine" refers to a vaccine comprising a peptide produced by synthesizing a viral antigen or an antigenic determinant only, chemically or by using recombinant DNA technology.

The term "genetically engineered vaccine" may refer to one in which a specific gene that causes virulence of the virus is modified or removed.

The vaccine of the present invention can be used as a mixed or complex vaccine for preventing other diseases along with influenza by mixing with inactivated microbes or antigens used in the production of other vaccines for preventing influenza.

The term "mixed vaccine" refers to a vaccine in which different virus vaccines are used together. The term "combined vaccine" refers to a vaccine in which a virus vaccine is combined with a bacterial vaccine.

In addition, a vaccine composition of the present invention may further comprise at least one selected from the group consisting of a solvent, an immunity enhancer (adjuvant) and an excipient. The solvent may include physiological saline or distilled water, and the immunity enhancer may include Freund's incomplete or complete adjuvant, aluminum hydroxide gel, and vegetable and mineral oil, etc. Further, the excipient may include, but not limited to, aluminum phosphate, aluminum hydroxide or aluminum potassium sulfate (alum). It may further comprise known materials used in preparing vaccines known to those of ordinary skill in the art.

The vaccine composition of the present invention may be prepared as oral or parenteral formulations. Preferably, it may be prepared as an injection solution, which is a parenteral formulation, and can be administered via the intradermal, intramuscular, intraperitoneal, intravenous, subcutaneous, nasal or epidural routes.

The present invention also provides a pharmaceutical composition for preventing or treating an influenza infectious disease comprising the polypeptide represented by residues 379 to 474 of SEQ ID NO: 1 or the polypeptide represented by SEQ ID NO: 3.

The polypeptide represented by residues 379 to 474 of SEQ ID NO: 1 or the polypeptide represented by SEQ ID NO: 3 induces an immune response by forming an antibody in an individual when administered to the individual, and thus can be effectively utilized in preventing or treating influenza infectious diseases.

The term "influenza virus disease," as used herein, refers to a pathological condition caused by the presence of an influenza virus, e. g., influenza A or B virus, or by invasion of influenza virus into a cell or an individual. In a specific embodiment, the term may refer to a respiratory disease caused by influenza virus. Preferably, it may be at least one selected from the group consisting of sinusitis, paroxysmal asthma, otitis media, cystic fibrosis, bronchitis, pneumonia and diarrhea.

A composition of the present invention is administered in a pharmaceutically effective amount. The term "pharmaceutically effective amount" refers to an amount sufficient to treat a disease at a reasonable benefit/risk ratio applicable to medical treatment. Effective dose level may be determined by the factors including the type and severity of an individual, age, sex, type of infectious virus, activity of the drug, sensitivity to the drug, time of administration, route of administration and rate of excretion, duration of treatment, and concomitantly used drug, and by the factors well-known in the medical field. The composition of the present invention may be administered as a single therapeutic agent or in combination with other therapeutic agent, and may be administered sequentially or simultaneously with a conventional therapeutic agent. And it may be administered in a single or multiple doses. It is important to take into account all of the above factors and to administer an amount capable of achieving the maximum effect in a minimal amount without side effects, which can be easily determined by those skilled in the art.

Further, the present invention provides a method for inducing influenza immunity comprising the step of administering to an individual the polypeptide represented by residues 379 to 474 of SEQ ID NO: 1 or the polypeptide represented by SEQ ID NO: 3.

The individual refers to an animal that has already been infected or can be infected with influenza virus. By administering the composition of the present invention to the individuals, animals infected with various influenza virus subtypes or variants can be treated. More specifically, the individual refers to any kind of animal that can propagate to an individual. The individual may be one other than a human.

Hereinafter, the present invention will be described in detail with reference to Preparation Examples and Examples. However, the following Preparation Examples and Examples are intended to illustrate the present invention and the scope of the present invention is not limited by the following Preparation Examples and Examples.

MODE FOR THE INVENTION

Example 1. Preparation of Single and Trimerized HA2 Helical Domain of Influenza Hemagglutinin In order to identify the sequence of influenza hemagglutinin (hereinafter, HA), which can be used as a versatile antigen, six sequences of the amino acid sequences of various subtypes of hemagglutinin protein were comparatively analyzed using a structure-based protein sequence analysis comparison program (Clustal W & ESPript 3.0), and the HA2 helical domain with a conserved sequence among the subtypes was determined. Results of the structure-based sequence analysis of the influenza hemagglutinin HA2 head and stem domains are shown in FIGS. 1 and 2. The HA2 helical domain having the commonly conserved amino acid sequence in hemagglutinin was identified through the above sequence analysis, which was used for preparing the following antigens.

Hemagglutinin protein (567 amino acids) of Influenza A virus (A/California/04/2009 (H1N1)) used in the experiment was synthesized by Bioneer Co., and its base sequence was shown as SEQ ID NO: 4. The HA2 helical domain (residues 379-474) having a commonly conserved amino acid sequence in hemagglutinin (A/California/04/2009 (H1N1), NCBI: FJ966082.1) represented by SEQ ID NO: 1 was subcloned into the NdeI and XhoI sites of pET21a, and overexpressed using *Escherichia coli* BL21 (DE3) RIL strain.

In order to prepare a trimerized HA2 helical domain, a fragment 1 of the amino acid residues 379-480 of HA2 helical domain (SEQ ID NO: 1), a fragment 2 of the amino acid residues 373-480 of SEQ ID NO: 1, and a fragment 3 of the amino acid residues 373-480 of SEQ ID NO: 1 were subcloned into pET28a by using NdeI and BamHI, BamHI and HindIII, and HindIII and XhoI, respectively, such that six histidines (SEQ ID NO: 10) may attach to the N- and C-terminals of the protein and overexpressed using *Escherichia coli* BL21(DE3) star strain. Each protein was inoculated into *Escherichia coli* and incubated at 291 K for 16 hours with 0.2 mM IPTG when O.D value was in the range of 0.6-0.8 at 600 nm. The used expression vector, pET28a-3XHA2HD, is shown in FIG. 3.

His-tagged single HA2 domain or trimerized HA2 helical domain was purified by nickel-affinity chromatography and dialyzed with a buffer solution containing 20 mM Tris-HCl (pH 7.5), 0.2 M NaCl, 5% (v/v) glycerol to obtain a purified single HA2 domain and trimerized HA2. The results are shown in FIG. 4(A) and FIG. 4(B).

As shown in FIG. 4(A) and FIG. 4(B), a single HA2 helical domain and its trimerized helical domain were identified on SDS-PAGE. It was also verified that the purity was 96% or more by nickel-affinity chromatography. The base sequence for expressing the trimerized HA2 helical domain is shown as SEQ ID NO: 2, and the 351 amino acid sequence prepared thereby is shown as SEQ ID NO: 3. Thereafter, the single HA2 helical domain and its trimerized helical domain thus prepared were used as antigens to examine whether they were useful as versatile influenza vaccines.

Example 2. Verification of Antibody Production Against Single HA2 Helical Domain and Trimerized HA2 Helical Domain In order to examine whether the single or trimerized HA2 helical domain antigen obtained in Example 1 can effectively induce antibodies, its antibody formation effect was investigated.

First, pre-immune serum was taken before each of these was injected into rats and used as a negative control. For primary immunization, 200 μg of purified single or trimerized HA2 helical domain antigen was mixed with complete freund's adjuvant (sigma), and injected via intraperitoneal (IP) route, and after two weeks, a first boosting was performed by mixing with complete freund's adjuvant (sigma). One week later, a primary blood was collected and subjected to ELISA test, followed by boosting and bleeding with one week interval. One week after a third boosting, bleeding was conducted from the hearts of the rats, and four weeks later, a final serum was separated to perform a final ELISA test. In the ELISA test, 100 ng of antigen was used per well. Immune serum was diluted in a ratio of 1:100 to 1:100,000 with 1×PBS and anti-mouse IgG-HRP (ABC5001) diluted in a ratio of 1:10,000 was used for secondary identification. Color development was detected at the optical density of 405 nm, to finally verify the immune antibody production, which is shown in FIG. 5.

As shown in FIG. 5, a single HA2 helical domain exhibited an immune antibody formation effect in all four rats. In addition, the trimerized HA2 helical domain exhibited the effects of much higher immunity than the single domain and superior antibody-formation effect in all four rats. This indicated that both the single HA2 helical domain and the trimerized HA2 helical domain can effectively induce antibodies in the individuals.

Example 3. Verification of Usefulness of Trimerized HA2 Helical Domain as a Versatile Vaccine Since it was verified that the recombinant trimerized HA2 helical domain exhibits excellent antibody-inducing effect, it was examined whether it can be utilized as a versatile vaccine for various influenza antigens. More specifically, mouse monoclonal antibodies were prepared using purified trimerized HA2 helical domain antigen. The ascites obtained from a total of two clones were used to detect the presence of recombinant hemagglutinin (pH1N1, cH3N2, hH3N2, aH5N1, dH7N9) expressed in an insect through Western blot. The results are shown in FIG. 6.

Figure 6:
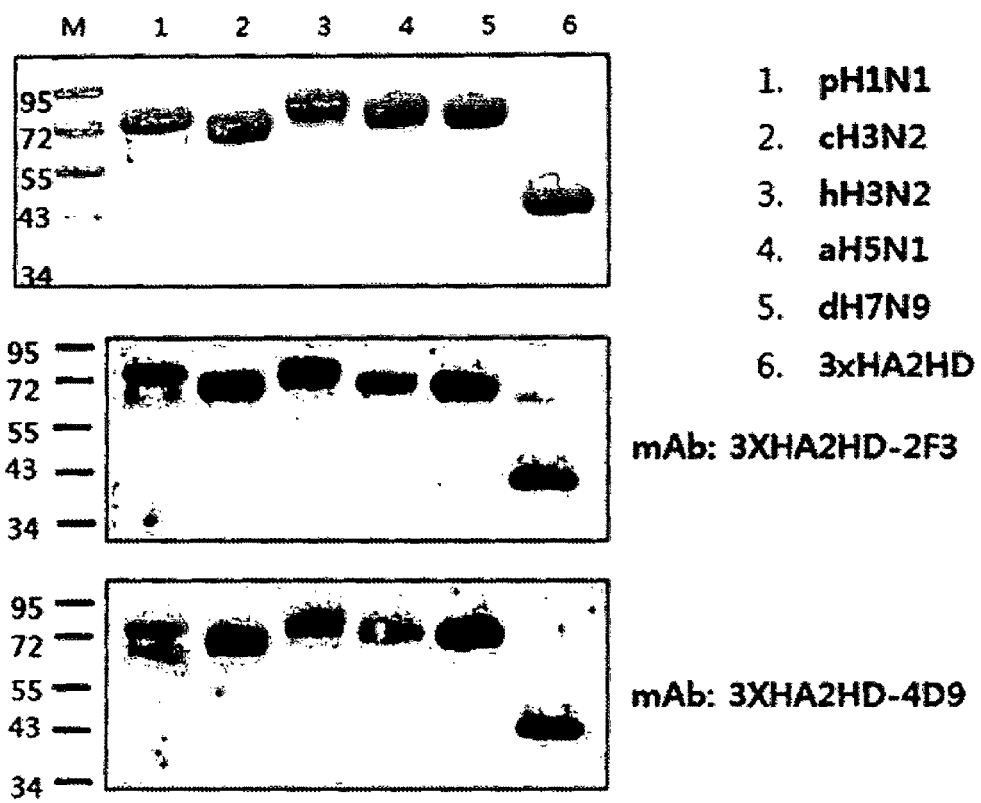
FIG. 6 shows the binding effects of the antibodies induced by trimerized HA2 helical domain (3XHA2HD) to influenza of pH1N1, cH3N2, hH3N2, aH5N1, and dH7N9 subtypes.

As shown in FIG. 6, it was found that the monoclonal antibodies to the trimerized HA2 helical domain bind to all of the various subtypes of hemagglutinin. Accordingly, it was verified that the trimerized HA2 helical domain can be utilized as a versatile vaccine for various subtypes.

Therefore, it was found that the single HA2 helical domain and its trimerized HA2 helical domain of the present invention function as antigens to effectively induce antibodies, and the antibodies are useful so that they show therapeutic effects against various subtypes of influenza.

INDUSTRIAL USABILITY

The polypeptide represented by SEQ ID NO: 3 and the polypeptide represented by residues 379 to 474 of SEQ ID NO: 1 of the present invention can be mass-produced in *E. coli*, and effectively produce neutralizing antibodies against various influenza virus subtypes, and thus, the polypeptides can be widely utilized as versatile vaccines for influenza virus subtypes and new influenza virus variants.

The invention claimed is:

1. An influenza virus vaccine composition comprising a polypeptide comprising SEQ ID NO: 3.

2. The vaccine composition of claim 1, wherein SEQ ID NO: 3 is encoded by the base sequence of SEQ ID NO: 2.

3. The vaccine composition of claim 1, wherein the polypeptide of SEQ ID NO: 3 is in a trimerized form.

4. The vaccine composition of claim 3, wherein the trimerized form comprises the following fragments (a)-(c):

(a) a fragment 1 consisting of residues 379-480 of SEQ ID NO: 1, (b) a fragment 2 consisting of residues 373-480 of SEQ ID NO: 1, and (c) a fragment 3 consisting of residues 373-480 of SEQ ID NO: 1.

5. The vaccine composition of claim 1, wherein the virus is of at least one influenza virus subtype selected from the group consisting of H1, H3, H5, H7 and H9.

6. The vaccine composition of claim 1, wherein the vaccine is a versatile vaccine.

7. The vaccine composition of claim 1, wherein the vaccine is at least one selected from the group consisting of a subunit vaccine, a synthetic vaccine, and a genetically engineered vaccine.

8. A pharmaceutical composition comprising a polypeptide comprising SEQ ID NO: 3 and a pharmaceutically acceptable carrier.

9. A method for inducing influenza immunity comprising a step of administering to an individual a polypeptide comprising SEQ ID NO: 3.

10. A method of treating or preventing disease related to or aggravated by influenza virus infection in a subject in need thereof comprising administering to the subject a composition comprising an isolated polypeptide comprising SEQ ID NO: 3 and a pharmaceutically acceptable carrier.

11. The method of claim 10, wherein the disease related to or aggravated by influenza infection is at least one selected from the group consisting of sinusitis, paroxysmal asthma, otitis media, cystic fibrosis, bronchitis, pneumonia and diarrhea.

* * * * *

SEQUENCE LISTING

```
<160> NUMBER OF SEQ ID NOS: 10

<210> SEQ ID NO 1
<211> LENGTH: 566
<212> TYPE: PRT
<213> ORGANISM: Influenza A virus

<400> SEQUENCE: 1

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Pro Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
    130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Ser Leu
        195                 200                 205

Tyr Gln Asn Ala Asp Thr Tyr Val Phe Val Gly Ser Ser Arg Tyr Ser
    210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
```

-continued

```
        275                 280                 285

Val His Asp Cys Asn Thr Thr Cys Gln Thr Pro Lys Gly Ala Ile Asn
    290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
        355                 360                 365

His His Gln Asn Glu Gln Gly Ser Gly Tyr Ala Ala Asp Leu Lys Ser
    370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Thr Arg Ile Tyr
        515                 520                 525

Gln Ile Leu Ala Ile Tyr Ser Thr Val Ala Ser Ser Leu Val Leu Val
    530                 535                 540

Val Ser Leu Gly Ala Ile Ser Phe Trp Met Cys Ser Asn Gly Ser Leu
545                 550                 555                 560

Gln Cys Arg Ile Cys Ile
                565

<210> SEQ ID NO 2
<211> LENGTH: 1056
<212> TYPE: DNA
<213> ORGANISM: Influenza A virus

<400> SEQUENCE: 2
atgggcagca gccatcatca tcatcatcac agcagcggcc tggtgccgcg cggcagccat      60
atggcagccg acctgaagag cacacagaat gccattgacg agattactaa caaagtaaat     120
tctgttattg aaaagatgaa tacacagttc acagcagtag gtaaagagtt caaccacctg     180
gaaaaaagaa tagagaattt aaataaaaaa gttgatgatg gtttcctgga catttggact     240
tacaatgccg aactgttggt tctattggaa aatgaaagaa ctttggacta ccacgattca     300
aatgtgaaga acttatatga aaaggtaaga agccagctaa aaaacaatgc caaggaaatt     360
ggaaacggcg gatccgagca ggggtcagga tatgcagccg acctgaagag cacacagaat     420
gccattgacg agattactaa caaagtaaat tctgttattg aaaagatgaa tacacagttc     480
```

```
acagcagtag gtaaagagtt caaccacctg gaaaaaagaa tagagaattt aaataaaaaa      540
gttgatgatg gtttcctgga catttggact tacaatgccg aactgttggt tctattggaa      600
aatgaaagaa ctttggacta ccacgattca aatgtgaaga acttatatga aaaggtaaga      660
agccagctaa aaacaatgc caaggaaatt ggaaacggca agcttgagca ggggtcagga       720
tatgcagccg acctgaagag cacacagaat gccattgacg agattactaa caaagtaaat      780
tctgttattg aaaagatgaa tacacagttc acagcagtag gtaaagagtt caaccacctg      840
gaaaaaagaa tagagaattt aaataaaaaa gttgatgatg gtttcctgga catttggact      900
tacaatgccg aactgttggt tctattggaa aatgaaagaa ctttggacta ccacgattca      960
aatgtgaaga acttatatga aaaggtaaga agccagctaa aaacaatgc caaggaaatt     1020 ggaaacggcc tcgagcacca ccaccaccac cactga                              1056
```

<210> SEQ ID NO 3
<211> LENGTH: 351
<212> TYPE: PRT
<213> ORGANISM: Influenza A virus

<400> SEQUENCE: 3

```
Met Gly Ser Ser His His His His His His Ser Ser Gly Leu Val Pro
1               5                   10                  15

Arg Gly Ser His Met Ala Ala Asp Leu Lys Ser Thr Gln Asn Ala Ile
            20                  25                  30

Asp Glu Ile Thr Asn Lys Val Asn Ser Val Ile Glu Lys Met Asn Thr
        35                  40                  45

Gln Phe Thr Ala Val Gly Lys Glu Phe Asn His Leu Glu Lys Arg Ile
    50                  55                  60

Glu Asn Leu Asn Lys Lys Val Asp Asp Gly Phe Leu Asp Ile Trp Thr
65                  70                  75                  80

Tyr Asn Ala Glu Leu Leu Val Leu Leu Glu Asn Glu Arg Thr Leu Asp
                85                  90                  95

Tyr His Asp Ser Asn Val Lys Asn Leu Tyr Glu Lys Val Arg Ser Gln
            100                 105                 110

Leu Lys Asn Asn Ala Lys Glu Ile Gly Asn Gly Gly Ser Glu Gln Gly
        115                 120                 125

Ser Gly Tyr Ala Ala Asp Leu Lys Ser Thr Gln Asn Ala Ile Asp Glu
    130                 135                 140

Ile Thr Asn Lys Val Asn Ser Val Ile Glu Lys Met Asn Thr Gln Phe
145                 150                 155                 160

Thr Ala Val Gly Lys Glu Phe Asn His Leu Glu Lys Arg Ile Glu Asn
                165                 170                 175

Leu Asn Lys Lys Val Asp Asp Gly Phe Leu Asp Ile Trp Thr Tyr Asn
            180                 185                 190

Ala Glu Leu Leu Val Leu Leu Glu Asn Glu Arg Thr Leu Asp Tyr His
        195                 200                 205

Asp Ser Asn Val Lys Asn Leu Tyr Glu Lys Val Arg Ser Gln Leu Lys
    210                 215                 220

Asn Asn Ala Lys Glu Ile Gly Asn Gly Lys Leu Glu Gln Gly Ser Gly
225                 230                 235                 240

Tyr Ala Ala Asp Leu Lys Ser Thr Gln Asn Ala Ile Asp Glu Ile Thr
                245                 250                 255

Asn Lys Val Asn Ser Val Ile Glu Lys Met Asn Thr Gln Phe Thr Ala
            260                 265                 270
```

```
Val Gly Lys Glu Phe Asn His Leu Glu Lys Arg Ile Glu Asn Leu Asn
        275                 280                 285

Lys Lys Val Asp Asp Gly Phe Leu Asp Ile Trp Thr Tyr Asn Ala Glu
        290                 295                 300

Leu Leu Val Leu Leu Glu Asn Glu Arg Thr Leu Asp Tyr His Asp Ser
305                 310                 315                 320

Asn Val Lys Asn Leu Tyr Glu Lys Val Arg Ser Gln Leu Lys Asn Asn
                325                 330                 335

Ala Lys Glu Ile Gly Asn Gly Leu Glu His His His His His His
                340                 345                 350

<210> SEQ ID NO 4
<211> LENGTH: 1701
<212> TYPE: DNA
<213> ORGANISM: Influenza A virus

<400> SEQUENCE: 4
```

| | | | | | |
|---|---|---|---|---|---|
| atgaaggcaa | tactagtagt | tctgctatat | acatttgcaa | ccgcaaatgc | agacacatta | 60 |
| tgtataggtt | atcatgcgaa | caattcaaca | gacactgtag | acacagtact | agaaaagaat | 120 |
| gtaacagtaa | cacactctgt | taaccttcta | aagacaagc | ataacgggaa | actatgcaaa | 180 |
| ctaagagggg | tagccccatt | gcatttgggt | aaatgtaaca | ttgctggctg | atcctggga | 240 |
| aatccagagt | gtgaatcact | ctccacagca | agctcatggt | cctacattgt | ggaaacacct | 300 |
| agttcagaca | tggaacgtg | ttacccagga | gatttcatcg | attatgagga | gctaagagag | 360 |
| caattgagct | cagtgtcatc | atttgaaagg | tttgagatat | tccccaagac | aagttcatgg | 420 |
| cccaatcatg | actcgaacaa | aggtgtaacg | gcagcatgtc | ctcatgctgg | agcaaaaagc | 480 |
| ttctacaaaa | atttaatatg | gctagttaaa | aaaggaaatt | cacccaaa | gctcagcaaa | 540 |
| tcctacatta | atgataaagg | gaaagaagtc | ctcgtgctat | ggggcattca | ccatccatct | 600 |
| actagtgctg | accaacaaag | tctctatcag | aatgcagata | catatgtttt | tgtgggtca | 660 |
| tcaagataca | gcaagaagtt | caagccggaa | atagcaataa | gacccaaagt | gagggatcaa | 720 |
| gaagggagaa | tgaactatta | ctggacacta | gtagagccgg | gagacaaaat | aacattcgaa | 780 |
| gcaactggaa | atctagtggt | accgagatat | gcattcgcaa | tggaaagaaa | tgctggatct | 840 |
| ggtattatca | tttcagatac | accagtccac | gattgcaata | caacttgtca | acacccaag | 900 |
| ggtgctataa | acaccagcct | cccatttcag | aatatacatc | cgatcacaat | ggaaaatgt | 960 |
| ccaaaatatg | taaaaagcac | aaaattgaga | ctggccacag | gattgaggaa | tatcccgtct | 1020 |
| attcaatcta | gaggcctatt | tggggccatt | gccggtttca | ttgaaggggg | gtggacaggg | 1080 |
| atggtagatg | gatggtacgg | ttatcaccat | caaaatgagc | aggggtcagg | atatgcagcc | 1140 |
| gacctgaaga | gcacacagaa | tgccattgac | gagattacta | acaaagtaaa | ttctgttatt | 1200 |
| gaaagatga | atacagtt | cacagcagta | ggtaaagagt | tcaaccacct | ggaaaaaaga | 1260 |
| atagagaatt | taaataaaaa | agttgatgat | ggtttcctgg | acatttggac | ttacaatgcc | 1320 |
| gaactgttgg | ttctattgga | aaatgaaaga | actttggact | accacgattc | aaatgtgaag | 1380 |
| aacttatatg | aaaaggtaag | aagccagcta | aaaaacaatg | ccaaggaaat | tggaaacggc | 1440 |
| tgctttgaat | tttaccacaa | atgcgataac | acgtgcatgg | aaagtgtcaa | aatgggact | 1500 |
| tatgactacc | caaatactc | agaggaagca | aaattaaaca | gagaagaaat | agatgggta | 1560 |
| aagctggaat | caacaaggat | ttaccagatt | ttggcgatct | attcaactgt | cgccagttca | 1620 |
| ttggtactgg | tagtctccct | gggggcaatc | agtttctgga | tgtgctctaa | tgggtctcta | 1680 | cagtgtagaa tatgtattta a                                                 1701

<210> SEQ ID NO 5
<211> LENGTH: 566
<212> TYPE: PRT
<213> ORGANISM: Influenza A virus

<400> SEQUENCE: 5

Met Lys Ala Asn Leu Leu Val Leu Leu Cys Ala Leu Ala Ala Ala Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Lys Cys Asn Ile Ala Gly Trp Leu Leu Gly
65                  70                  75                  80

Asn Pro Glu Cys Asp Pro Leu Leu Pro Val Arg Ser Trp Ser Tyr Ile
                85                  90                  95

Val Glu Thr Pro Asn Ser Glu Asn Gly Ile Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Asn
    130                 135                 140

Thr Thr Lys Gly Val Thr Ala Ala Cys Ser His Ala Gly Lys Ser Ser
145                 150                 155                 160

Phe Tyr Arg Asn Leu Leu Trp Leu Thr Glu Lys Glu Gly Ser Tyr Pro
                165                 170                 175

Lys Leu Lys Asn Ser Tyr Val Asn Lys Lys Gly Lys Glu Val Leu Val
            180                 185                 190

Leu Trp Gly Ile His His Pro Ser Asn Ser Lys Asp Gln Gln Asn Ile
        195                 200                 205

Tyr Gln Asn Glu Asn Ala Tyr Val Ser Val Val Thr Ser Asn Tyr Asn
    210                 215                 220

Arg Arg Phe Thr Pro Glu Ile Ala Glu Arg Pro Lys Val Arg Asp Gln
225                 230                 235                 240

Ala Gly Arg Met Asn Tyr Tyr Trp Thr Leu Leu Lys Pro Gly Asp Thr
                245                 250                 255

Ile Ile Phe Glu Ala Asn Gly Asn Leu Ile Ala Pro Arg Tyr Ala Phe
            260                 265                 270

Ala Leu Ser Arg Gly Phe Gly Ser Gly Ile Ile Thr Ser Asn Ala Ser
        275                 280                 285

Met His Glu Cys Asn Thr Lys Cys Gln Thr Pro Leu Gly Ala Ile Asn
    290                 295                 300

Ser Ser Leu Pro Phe Gln Asn Ile His Pro Val Thr Ile Gly Glu Cys
305                 310                 315                 320

Pro Lys Tyr Val Arg Ser Ala Lys Leu Arg Met Val Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
        370                 375                 380

Thr Gln Asn Ala Ile Asn Gly Ile Thr Asn Lys Val Asn Ser Val Ile
385                 390                 395                 400

Glu Lys Met Asn Ile Gln Phe Thr Ala Val Gly Lys Glu Phe Asn Lys
                405                 410                 415

Leu Glu Lys Arg Met Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Phe His Asp Ser Asn Val Lys Asn Leu Tyr Glu
    450                 455                 460

Lys Val Lys Ser Gln Leu Lys Asn Asn Ala Lys Glu Ile Gly Asn Gly
465                 470                 475                 480

Cys Phe Glu Phe Tyr His Lys Cys Asp Asn Glu Cys Met Glu Ser Val
                485                 490                 495

Arg Asn Gly Thr Tyr Asp Tyr Pro Lys Tyr Ser Glu Glu Ser Lys Leu
            500                 505                 510

Asn Arg Glu Lys Val Asp Gly Val Lys Leu Glu Ser Met Gly Ile Tyr
        515                 520                 525

Gln Ile Leu Ala Ile Tyr Ser Thr Val Ala Ser Ser Leu Val Leu Leu
    530                 535                 540

Val Ser Leu Gly Ala Ile Ser Phe Trp Met Cys Ser Asn Gly Ser Leu
545                 550                 555                 560

Gln Cys Arg Ile Cys Ile
                565

<210> SEQ ID NO 6
<211> LENGTH: 566
<212> TYPE: PRT
<213> ORGANISM: Influenza A virus

<400> SEQUENCE: 6

Met Lys Thr Val Ile Ala Leu Ser Tyr Ile Phe Cys Leu Ala Phe Gly
1               5                   10                  15

Gln Asn Leu Pro Gly Asn Glu Asn Asn Ala Ala Thr Leu Cys Leu Gly
            20                  25                  30

His His Ala Val Pro Asn Gly Thr Ile Val Lys Thr Ile Thr Asp Asp
        35                  40                  45

Gln Ile Glu Val Thr Asn Ala Thr Glu Leu Val Gln Asn Ser Ser Thr
    50                  55                  60

Gly Lys Ile Cys Asn Asn Pro His Lys Ile Leu Asp Gly Arg Asp Cys
65                  70                  75                  80

Thr Leu Ile Asp Ala Leu Leu Gly Asp Pro His Cys Asp Val Phe Gln
                85                  90                  95

Asn Glu Thr Trp Asp Leu Phe Val Glu Arg Ser Asn Ala Phe Ser Asn
            100                 105                 110

Cys Tyr Pro Tyr Asp Val Pro Asp Tyr Ala Ser Leu Arg Ser Ile Val
        115                 120                 125

Ala Ser Ser Gly Thr Leu Glu Phe Ile Thr Glu Gly Phe Thr Trp Thr
    130                 135                 140

Gly Val Thr Gln Asn Gly Gly Ser Gly Ala Cys Lys Arg Gly Pro Ala
145                 150                 155                 160

Asn Gly Phe Phe Ser Arg Leu Asn Trp Leu Thr Lys Ser Gly Asn Thr

-continued

```
                165                 170                 175
Tyr Pro Val Leu Asn Val Thr Met Pro Asn Asn Asn Phe Asp Lys
            180                 185                 190
Leu Tyr Ile Trp Gly Val His His Pro Ser Thr Asn Gln Glu Gln Thr
            195                 200                 205
Ser Leu Tyr Ile Gln Ala Ser Gly Arg Val Thr Val Ser Thr Arg Arg
    210                 215                 220
Ser Gln Gln Thr Ile Ile Pro Asn Ile Gly Ser Arg Pro Leu Val Arg
225                 230                 235                 240
Gly Gln Ser Gly Arg Ile Ser Val Tyr Trp Thr Ile Val Lys Pro Gly
                245                 250                 255
Asp Val Leu Val Ile Asn Ser Asn Gly Asn Leu Ile Ala Pro Arg Gly
                260                 265                 270
Tyr Phe Lys Met Arg Ile Gly Lys Ser Ser Ile Met Arg Ser Asp Ala
            275                 280                 285
Pro Ile Asp Thr Cys Ile Ser Glu Cys Ile Thr Pro Asn Gly Ser Ile
    290                 295                 300
Pro Asn Asp Lys Pro Phe Gln Asn Val Asn Lys Ile Thr Tyr Gly Ala
305                 310                 315                 320
Cys Pro Lys Tyr Val Lys Gln Asn Thr Leu Lys Leu Ala Thr Gly Met
                325                 330                 335
Arg Asn Val Pro Glu Arg Gln Thr Arg Gly Leu Phe Gly Ala Ile Ala
            340                 345                 350
Gly Phe Ile Glu Asn Gly Trp Glu Gly Met Val Asp Gly Trp Tyr Gly
            355                 360                 365
Phe Arg His Gln Asn Ser Glu Gly Thr Gly Gln Ala Ala Asp Leu Lys
    370                 375                 380
Ser Thr Gln Ala Ala Ile Asp Gln Ile Asn Gly Lys Leu Asn Arg Val
385                 390                 395                 400
Ile Glu Lys Thr Asn Glu Lys Phe His Gln Ile Glu Lys Glu Phe Ser
                405                 410                 415
Glu Val Glu Gly Arg Ile Gln Asp Leu Glu Arg Tyr Val Glu Asp Thr
            420                 425                 430
Lys Val Asp Leu Trp Ser Tyr Asn Ala Glu Leu Leu Val Ala Leu Glu
            435                 440                 445
Asn Gln Lys Thr Ile Asp Leu Thr Asp Ser Glu Met Asn Lys Leu Phe
    450                 455                 460
Glu Lys Thr Arg Arg Gln Leu Arg Glu Asn Ala Glu Asp Met Gly Asn
465                 470                 475                 480
Gly Cys Phe Lys Ile Tyr His Lys Cys Asp Asn Ala Cys Ile Glu Ser
                485                 490                 495
Ile Arg Asn Gly Thr Tyr Asp His Asn Ile Tyr Arg Asp Glu Ala Val
            500                 505                 510
Asn Asn Arg Phe Gln Ile Lys Gly Val Glu Leu Lys Ser Gly Tyr Lys
            515                 520                 525
Asp Trp Ile Leu Trp Ile Ser Phe Ala Ile Ser Cys Phe Leu Leu Cys
    530                 535                 540
Val Val Leu Leu Gly Phe Ile Met Trp Ala Cys Gln Arg Gly Asn Ile
545                 550                 555                 560
Arg Cys Asn Ile Cys Ile
                565

<210> SEQ ID NO 7
```

```
<211> LENGTH: 533
<212> TYPE: PRT
<213> ORGANISM: Influenza A virus
<220> FEATURE:
<221> NAME/KEY: MOD_RES
<222> LOCATION: (306)..(306)
<223> OTHER INFORMATION: Any amino acid

<400> SEQUENCE: 7
```

| | | | | | | | | | | | | | | |
|---|---|---|---|---|---|---|---|---|---|---|---|---|---|---|
| Met | Glu | Lys | Asn | Val | Thr | Val | Thr | His | Ala | Gln | Asp | Ile | Leu | Glu | Lys |
| 1 | | | | 5 | | | | | 10 | | | | | 15 | |

| Thr | His | Asn | Gly | Lys | Leu | Cys | Asp | Leu | Asp | Gly | Val | Lys | Pro | Leu | Ile |
| | | | 20 | | | | | 25 | | | | | 30 | | |

| Leu | Arg | Asp | Cys | Ser | Val | Ala | Gly | Trp | Leu | Leu | Gly | Asn | Pro | Met | Cys |
| | | 35 | | | | | 40 | | | | | 45 | | | |

| Asp | Glu | Phe | Ile | Asn | Val | Pro | Glu | Trp | Ser | Tyr | Ile | Val | Glu | Lys | Ala |
| | 50 | | | | | 55 | | | | | 60 | | | | |

| Asn | Pro | Pro | Asn | Asp | Leu | Cys | Tyr | Pro | Gly | Asn | Phe | Asn | Asp | Tyr | Glu |
| 65 | | | | | 70 | | | | | 75 | | | | | 80 |

| Glu | Leu | Lys | His | Leu | Leu | Ser | Arg | Ile | Asn | His | Phe | Glu | Lys | Ile | Gln |
| | | | | 85 | | | | | 90 | | | | | 95 | |

| Ile | Ile | Pro | Lys | Ser | Ser | Trp | Ser | Asp | His | Glu | Ala | Ser | Ser | Gly | Val |
| | | | 100 | | | | | 105 | | | | | 110 | | |

| Ser | Ser | Ala | Cys | Pro | Tyr | Gln | Gly | Arg | Ser | Ser | Phe | Phe | Arg | Asn | Val |
| | | 115 | | | | | 120 | | | | | 125 | | | |

| Val | Trp | Leu | Ile | Lys | Lys | Asn | Ser | Ala | Tyr | Pro | Thr | Ile | Lys | Arg | Ser |
| | 130 | | | | | 135 | | | | | 140 | | | | |

| Tyr | Asn | Asn | Thr | Asn | Gln | Glu | Asp | Leu | Leu | Val | Leu | Trp | Gly | Ile | His |
| 145 | | | | | 150 | | | | | 155 | | | | | 160 |

| His | Pro | Asn | Asp | Ala | Ala | Glu | Gln | Thr | Arg | Leu | Tyr | Gln | Asn | Pro | Thr |
| | | | | 165 | | | | | 170 | | | | | 175 | |

| Thr | Tyr | Ile | Ser | Val | Gly | Thr | Ser | Thr | Leu | Asn | Gln | Arg | Leu | Val | Pro |
| | | | 180 | | | | | 185 | | | | | 190 | | |

| Lys | Ile | Ala | Thr | Arg | Ser | Lys | Val | Asn | Gly | Gln | Ser | Gly | Arg | Met | Glu |
| | | 195 | | | | | 200 | | | | | 205 | | | |

| Phe | Phe | Trp | Thr | Ile | Leu | Lys | Pro | Asn | Asp | Ala | Ile | Ser | Phe | Glu | Ser |
| | 210 | | | | | 215 | | | | | 220 | | | | |

| Asn | Gly | Asn | Phe | Ile | Ala | Pro | Glu | Tyr | Ala | Tyr | Lys | Ile | Val | Lys | Lys |
| 225 | | | | | 230 | | | | | 235 | | | | | 240 |

| Gly | Asp | Ser | Ala | Ile | Met | Lys | Ser | Glu | Leu | Glu | Tyr | Gly | Asn | Cys | Asn |
| | | | | 245 | | | | | 250 | | | | | 255 | |

| Thr | Lys | Cys | Gln | Thr | Pro | Met | Gly | Ala | Ile | Asn | Ser | Ser | Met | Pro | Phe |
| | | | 260 | | | | | 265 | | | | | 270 | | |

| His | Asn | Ile | His | Pro | Leu | Thr | Ile | Gly | Glu | Cys | Pro | Lys | Tyr | Val | Lys |
| | | 275 | | | | | 280 | | | | | 285 | | | |

| Ser | Ser | Arg | Leu | Val | Leu | Ala | Thr | Gly | Leu | Arg | Asn | Ser | Pro | Gln | Arg |
| | 290 | | | | | 295 | | | | | 300 | | | | |

| Glu | Xaa | Lys | Arg | Lys | Lys | Arg | Gly | Leu | Phe | Gly | Ala | Ile | Ala | Gly | Phe |
| 305 | | | | | 310 | | | | | 315 | | | | | 320 |

| Ile | Glu | Gly | Gly | Trp | Gln | Gly | Met | Val | Asp | Gly | Trp | Tyr | Gly | Tyr | His |
| | | | | 325 | | | | | 330 | | | | | 335 | |

| His | Ser | Asn | Glu | Gln | Gly | Ser | Gly | Tyr | Ala | Ala | Asp | Lys | Glu | Ser | Thr |
| | | | 340 | | | | | 345 | | | | | 350 | | |

| Gln | Lys | Ala | Ile | Asp | Gly | Val | Thr | Asn | Lys | Val | Asn | Ser | Ile | Ile | Asp |
| | | 355 | | | | | 360 | | | | | 365 | | | |

```
Lys Met Asn Thr Gln Phe Glu Ala Val Gly Arg Glu Phe Asn Asn Leu
    370                 375                 380
Glu Arg Arg Ile Glu Asn Leu Asn Lys Lys Met Glu Asp Gly Phe Leu
385                 390                 395                 400
Asp Val Trp Thr Tyr Asn Ala Glu Leu Leu Val Leu Met Glu Asn Glu
                405                 410                 415
Arg Thr Leu Asp Phe His Asp Ser Asn Val Lys Asn Leu Tyr Asp Lys
            420                 425                 430
Val Arg Leu Gln Leu Arg Asp Asn Ala Lys Glu Leu Gly Asn Gly Cys
        435                 440                 445
Phe Glu Phe Tyr His Arg Cys Asp Asn Glu Cys Ile Glu Ser Val Arg
    450                 455                 460
Asn Gly Thr Tyr Asp Tyr Pro Gln Tyr Ser Glu Glu Ala Arg Leu Lys
465                 470                 475                 480
Arg Glu Glu Ile Ser Gly Val Lys Leu Glu Ser Ile Gly Thr Tyr Gln
                485                 490                 495
Ile Leu Ser Ile Tyr Ser Thr Val Ala Ser Ser Leu Ala Leu Ala Ile
            500                 505                 510
Met Val Ala Gly Leu Ser Leu Trp Met Cys Ser Asn Gly Ser Leu Gln
        515                 520                 525
Cys Arg Ile Cys Ile
    530

<210> SEQ ID NO 8
<211> LENGTH: 560
<212> TYPE: PRT
<213> ORGANISM: Influenza A virus

<400> SEQUENCE: 8

Met Asn Thr Gln Ile Leu Val Phe Ala Leu Ile Ala Ile Ile Pro Thr
1               5                   10                  15
Asn Ala Asp Lys Ile Cys Leu Gly His His Ala Val Ser Asn Gly Thr
                20                  25                  30
Lys Val Asn Thr Leu Thr Glu Arg Gly Val Glu Val Val Asn Ala Thr
            35                  40                  45
Glu Thr Val Glu Arg Thr Asn Ile Pro Arg Ile Cys Ser Lys Gly Lys
    50                  55                  60
Arg Thr Val Asp Leu Gly Gln Cys Gly Leu Leu Gly Thr Ile Thr Gly
65                  70                  75                  80
Pro Pro Gln Cys Asp Gln Phe Leu Glu Phe Ser Ala Asp Leu Ile Ile
                85                  90                  95
Glu Arg Arg Glu Gly Ser Asp Val Cys Tyr Pro Gly Lys Phe Val Asn
            100                 105                 110
Glu Glu Ala Leu Arg Gln Ile Leu Arg Glu Ser Gly Gly Ile Asp Lys
        115                 120                 125
Glu Ala Met Gly Phe Thr Tyr Ser Gly Ile Arg Thr Asn Gly Ala Thr
    130                 135                 140
Ser Ala Cys Arg Arg Ser Gly Ser Ser Phe Tyr Ala Glu Met Lys Trp
145                 150                 155                 160
Leu Leu Ser Asn Thr Asp Asn Ala Ala Phe Pro Gln Met Thr Lys Ser
                165                 170                 175
Tyr Lys Asn Thr Arg Lys Ser Pro Ala Leu Ile Val Trp Gly Ile His
            180                 185                 190
His Ser Val Ser Thr Ala Glu Gln Thr Lys Leu Tyr Gly Ser Gly Asn
        195                 200                 205
```

```
Lys Leu Val Thr Val Gly Ser Ser Asn Tyr Gln Gln Ser Phe Val Pro
210                 215                 220
Ser Pro Gly Ala Arg Pro Gln Val Asn Gly Ile Ser Gly Arg Ile Asp
225                 230                 235                 240
Phe His Trp Leu Met Leu Asn Pro Asn Asp Thr Val Thr Phe Ser Phe
                245                 250                 255
Asn Gly Ala Phe Ile Ala Pro Asp Arg Ala Ser Phe Leu Arg Gly Lys
                260                 265                 270
Ser Met Gly Ile Gln Ser Gly Val Gln Val Asp Ala Asn Cys Glu Gly
                275                 280                 285
Asp Cys Tyr His Ser Gly Gly Thr Ile Ile Ser Asn Leu Pro Phe Gln
290                 295                 300
Asn Ile Asp Ser Arg Ala Val Gly Lys Cys Pro Arg Tyr Val Lys Gln
305                 310                 315                 320
Arg Ser Leu Leu Leu Ala Thr Gly Met Lys Asn Val Pro Glu Ile Pro
                325                 330                 335
Lys Gly Arg Gly Leu Phe Gly Ala Ile Ala Gly Phe Ile Glu Asn Gly
                340                 345                 350
Trp Glu Gly Leu Ile Asp Gly Trp Tyr Gly Phe Arg His Gln Asn Ala
                355                 360                 365
Gln Gly Glu Gly Thr Ala Ala Asp Tyr Lys Ser Thr Gln Ser Ala Ile
370                 375                 380
Asp Gln Ile Thr Gly Lys Leu Asn Arg Leu Ile Glu Lys Thr Asn Gln
385                 390                 395                 400
Gln Phe Glu Leu Ile Asp Asn Glu Phe Asn Glu Val Glu Lys Gln Ile
                405                 410                 415
Gly Asn Val Ile Asn Trp Thr Arg Asp Ser Ile Thr Glu Val Trp Ser
                420                 425                 430
Tyr Asn Ala Glu Leu Leu Val Ala Met Glu Asn Gln His Thr Ile Asp
                435                 440                 445
Leu Ala Asp Ser Glu Met Asp Lys Leu Tyr Glu Arg Val Lys Arg Gln
450                 455                 460
Leu Arg Glu Asn Ala Glu Glu Asp Gly Thr Gly Cys Phe Glu Ile Phe
465                 470                 475                 480
His Lys Cys Asp Asp Asp Cys Met Ala Ser Ile Arg Asn Asn Thr Tyr
                485                 490                 495
Asp His Ser Lys Tyr Arg Glu Glu Ala Met Gln Asn Arg Ile Gln Ile
                500                 505                 510
Asp Pro Val Lys Leu Ser Ser Gly Tyr Lys Asp Val Ile Leu Trp Phe
                515                 520                 525
Ser Phe Gly Ala Ser Cys Phe Ile Leu Leu Ala Ile Val Met Gly Leu
530                 535                 540
Val Phe Ile Cys Val Lys Asn Gly Asn Met Arg Cys Thr Ile Cys Ile
545                 550                 555                 560

<210> SEQ ID NO 9
<211> LENGTH: 560
<212> TYPE: PRT
<213> ORGANISM: Influenza A virus

<400> SEQUENCE: 9

Met Glu Ile Ile Ala Leu Ile Ala Ile Leu Val Val Thr Gly Thr Ser
1               5                   10                  15

Asp Ala Asp Lys Ile Cys Ile Gly Tyr Gln Ser Thr Asn Ser Thr Glu
```

```
            20                  25                  30
Thr Val Asp Thr Leu Val Glu Asn Asn Val Pro Val Thr His Thr Lys
            35                  40                  45
Glu Leu Leu His Thr Glu His Asn Gly Met Leu Cys Ala Thr Asn Leu
        50                  55                  60
Gly His Pro Leu Ile Leu Asp Thr Cys Thr Ile Glu Gly Leu Val Tyr
65                  70                  75                  80
Gly Asn Pro Ser Cys Asp Leu Leu Gly Gly Lys Glu Trp Ser Tyr
                85                  90                  95
Ile Val Glu Arg Ser Ser Ala Val Asn Gly Met Cys Tyr Pro Gly Arg
                100                 105                 110
Val Glu Asn Leu Glu Glu Leu Arg Ser Phe Phe Ser Ser Ala Arg Ser
            115                 120                 125
Tyr Lys Arg Leu Leu Phe Pro Asp Arg Thr Trp Asn Val Thr Phe
        130                 135                 140
Thr Gly Thr Ser Lys Ala Cys Ser Gly Ser Phe Tyr Arg Ser Met Arg
145                 150                 155                 160
Trp Leu Thr His Lys Asn Asn Ser Tyr Pro Ile Gln Asp Ala Gln Tyr
                165                 170                 175
Thr Asn Asp Trp Gly Lys Asn Ile Leu Phe Met Trp Gly Ile His His
                180                 185                 190
Pro Pro Thr Asp Thr Glu Gln Met Asn Leu Tyr Lys Lys Ala Asp Thr
            195                 200                 205
Thr Thr Ser Ile Thr Thr Glu Asp Ile Asn Arg Thr Phe Lys Pro Val
        210                 215                 220
Ile Gly Pro Arg Pro Leu Val Asn Gly Gln Gln Gly Arg Ile Asp Tyr
225                 230                 235                 240
Tyr Trp Ser Val Leu Lys Pro Gly Gln Thr Leu Arg Ile Arg Ser Asn
                245                 250                 255
Gly Asn Leu Ile Ala Pro Trp Tyr Gly His Ile Leu Ser Gly Glu Ser
                260                 265                 270
His Gly Arg Ile Leu Lys Thr Asp Leu Asn Ser Gly Asn Cys Ile Ile
            275                 280                 285
Gln Cys Gln Thr Glu Lys Gly Gly Leu Asn Thr Thr Leu Pro Phe Gln
        290                 295                 300
Asn Val Ser Lys Tyr Ala Phe Gly Asn Cys Pro Lys Tyr Val Gly Val
305                 310                 315                 320
Lys Ser Leu Lys Leu Ala Val Gly Leu Arg Asn Val Pro Ala Thr Ser
                325                 330                 335
Gly Arg Gly Leu Phe Gly Ala Ile Ala Gly Phe Ile Glu Gly Gly Trp
                340                 345                 350
Pro Gly Leu Val Ala Gly Trp Tyr Gly Phe Gln His Ser Asn Asp Gln
            355                 360                 365
Gly Val Gly Ile Ala Ala Asp Lys Glu Ser Thr Gln Glu Ala Val Asp
        370                 375                 380
Lys Ile Thr Ser Lys Val Asn Asn Ile Ile Asp Lys Met Asn Lys Gln
385                 390                 395                 400
Tyr Glu Ile Ile Asp His Glu Phe Ser Glu Ile Glu Ala Arg Leu Asn
                405                 410                 415
Met Ile Asn Asn Lys Ile Asp Asp Gln Ile Gln Asp Ile Trp Ala Tyr
                420                 425                 430
Asn Ala Glu Leu Leu Val Leu Leu Glu Asn Gln Lys Thr Leu Asp Glu
            435                 440                 445
```

-continued

```
His Asp Ala Asn Val Asn Asn Leu Tyr Asn Lys Val Lys Arg Ala Leu
    450                 455                 460

Gly Ser Asn Ala Ile Glu Asp Gly Lys Gly Cys Phe Glu Leu Tyr His
465                 470                 475                 480

Lys Cys Asp Asp Gln Cys Met Glu Thr Ile Arg Asn Gly Thr Tyr Asp
                485                 490                 495

Arg Leu Lys Tyr Lys Glu Glu Ser Lys Leu Glu Arg Gln Lys Ile Glu
            500                 505                 510

Gly Val Lys Leu Glu Ser Glu Glu Thr Tyr Lys Ile Leu Thr Ile Tyr
        515                 520                 525

Ser Thr Val Ala Ser Ser Leu Val Leu Ala Ile Gly Leu Ala Ala Phe
    530                 535                 540

Met Phe Trp Ala Met Ser Asn Gly Ser Cys Arg Cys Asn Ile Cys Ile
545                 550                 555                 560

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 10

His His His His His His
1               5
```